(12) United States Patent
Kubo et al.

(10) Patent No.: US 8,920,831 B2
(45) Date of Patent: Dec. 30, 2014

(54) LIDOCAINE-CONTAINING HYDROGEL PATCH

(75) Inventors: Junichi Kubo, Tosu (JP); Seiichiro Tsuru, Tosu (JP); Keiichiro Tsurushima, Tosu (JP); Shinji Yamasoto, Tosu (JP)

(73) Assignee: Hisamitsu Pharmaceutical Co., Inc., Tosu-shi (JP)

( * ) Notice: Subject to any disclaimer, the term of this patent is extended or adjusted under 35 U.S.C. 154(b) by 0 days.

(21) Appl. No.: 14/127,322

(22) PCT Filed: Jun. 13, 2012

(86) PCT No.: PCT/JP2012/065079
§ 371 (c)(1),
(2), (4) Date: Dec. 18, 2013

(87) PCT Pub. No.: WO2012/176668
PCT Pub. Date: Dec. 27, 2012

(65) Prior Publication Data
US 2014/0141056 A1    May 22, 2014

(30) Foreign Application Priority Data

Jun. 20, 2011 (JP) ................................ 2011-136656

(51) Int. Cl.
| A61K 9/70 | (2006.01) |
| A61K 31/167 | (2006.01) |
| A61K 47/42 | (2006.01) |
| A61K 47/12 | (2006.01) |

(52) U.S. Cl.
CPC .............. *A61K 9/7046* (2013.01); *A61K 47/12* (2013.01); *A61K 47/42* (2013.01); *A61K 31/167* (2013.01); *A61K 9/7061* (2013.01); *A61K 9/7023* (2013.01); *A61K 9/7038* (2013.01)
USPC .......................................... 424/443; 514/626

(58) Field of Classification Search
CPC ......................... A61K 9/7023; A61K 9/7038
See application file for complete search history.

(56) References Cited

U.S. PATENT DOCUMENTS

| 3,108,995 | A | * | 10/1963 | Tourtellotte et al. .......... 530/354 |
| 5,827,529 | A | * | 10/1998 | Ono et al. ..................... 424/448 |
| 6,239,177 | B1 | * | 5/2001 | Mori et al. ..................... 514/563 |
| 6,429,228 | B1 | | 8/2002 | Inagi et al. |
| 2010/0234471 | A1 | | 9/2010 | Ishibashi et al. |
| 2010/0256174 | A1 | | 10/2010 | Yamaguchi et al. |

FOREIGN PATENT DOCUMENTS

| JP | 4 305523 | 10/1992 |
| JP | 2001 503035 | 3/2001 |
| JP | 2008 266198 | 11/2008 |
| WO | 2009 060629 | 5/2009 |
| WO | 2009 066457 | 5/2009 |
| WO | 2011 118604 | 9/2011 |

OTHER PUBLICATIONS

International Search Report issued Jul. 10, 2012 in PCT/JP12/065079 Filed Jun. 13, 2012.

* cited by examiner

*Primary Examiner* — Frederick Krass
*Assistant Examiner* — Isaac Shomer
(74) *Attorney, Agent, or Firm* — Oblon, Spivak, McClelland, Maier & Neustadt, L.L.P.

(57) ABSTRACT

A lidocaine-containing hydrogel patch comprising:
   a support layer; and
   a adhesive layer stacked on a surface of the support layer, wherein
   the adhesive layer comprises at least one selected from the group consisting of lidocaine and pharmaceutically acceptable salts thereof,
   a total content of the lidocaine and the pharmaceutically acceptable salts thereof is 3 to 8% by mass relative to an entire mass of the adhesive layer,
   the adhesive layer further comprises oleic acid in an amount of 0.3 to 1% by mass relative to the entire mass of the adhesive layer, and
   a pH of the adhesive layer is 6.8 to 7.4.

20 Claims, 1 Drawing Sheet

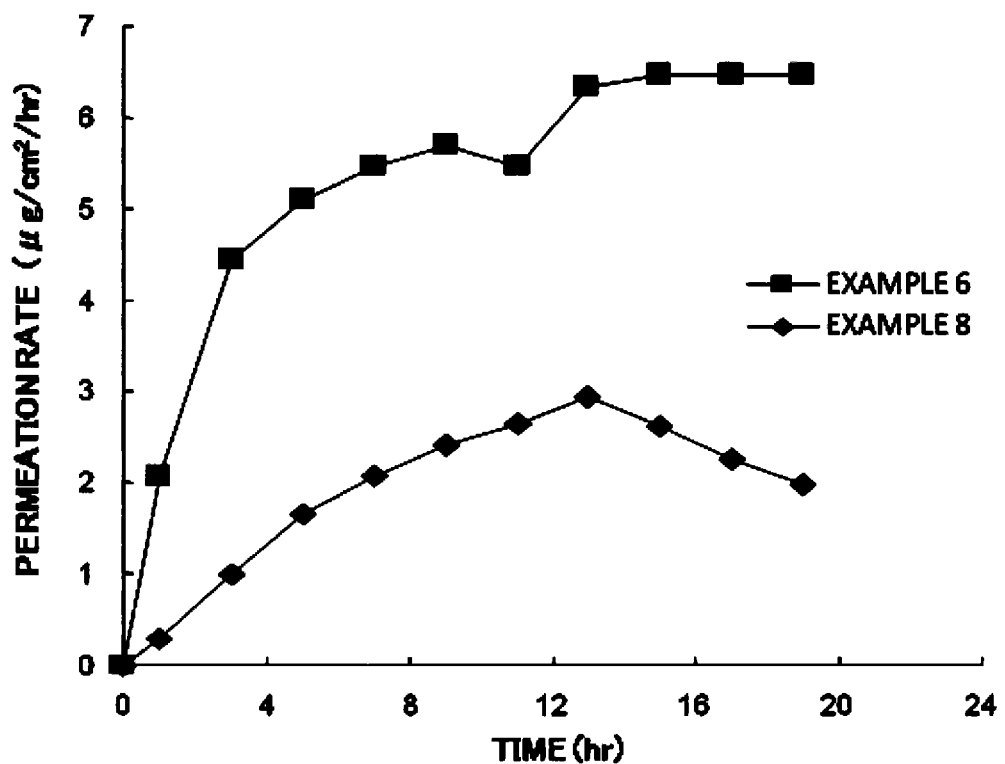

LIDOCAINE-CONTAINING HYDROGEL PATCH

TECHNICAL FIELD

The present invention relates to a lidocaine-containing hydrogel patch.

BACKGROUND ART

Currently, external preparations containing lidocaine having a local anesthetic effect are marketed for the purpose of alleviating, for example, nerve pain caused by herpes zoster, and development of such external preparations containing lidocaine is being advanced.

For example, Japanese Unexamined Patent Application Publication No. Hei 4-305523 (PTL 1) discloses a hydrogel patch for external use comprising an adhesive gel base containing lidocaine, wherein the adhesive gel base comprises a water-soluble high molecular weight substance, water and a water-retaining agent as essential ingredients. PTL 1 also states that the pH of the gel base is preferably in the range from 5 to 9, and that the gel base may comprises a conventional absorbing agent from the viewpoints of skin irritancy and stability. PTL 1 shows oleic acid and the like as examples of the absorbing agent.

Moreover, International Application Japanese-Phase Publication No. 2001-503035 (PTL 2) discloses a local anesthetic for external use containing: an active ingredient such as lidocaine; water; a lower alcohol such as ethanol; and a percutaneous absorption accelerator. PTL 2 shows fatty acids such as oleic acid as examples of the percutaneous absorption accelerator, and states that the pH of the local anesthetic for external use is preferably in the range from 6.0 to 8.5.

CITATION LIST

Patent Literatures

[PTL 1] Japanese Unexamined Patent Application Publication No. Hei 4-305523
[PTL 2] International Application Japanese-Phase Publication No. 2001-503035

SUMMARY OF INVENTION

Technical Problem

The present inventors have found a problem that lidocaine in the gel base of the conventional lidocaine-containing hydrogel patch for external use as described in PTL 1 crystallizes and precipitates over time. Note that the skin permeability of lidocaine is improved to some degree in the hydrogel patch disclosed in PTL 1, but PTL 1 does not mention the precipitation of crystals of lidocaine over time at all. Meanwhile, the skin permeability of lidocaine is improved to some degree in the external preparation such as a gel agent disclosed in PTL 2. However, PTL 2 does not specifically disclose application of the external preparation to a hydrogel patch, and does not mention the precipitation of crystals of lidocaine over time at all.

The present invention has been made in view of the above-described problem of the conventional technologies, and an object of the invention is to provide a lidocaine-containing hydrogel patch which is excellent in the skin permeability of lidocaine and which makes it possible to sufficiently suppress the precipitation of crystals of lidocaine over time.

Solution to Problem

The present inventors have conducted earnest study to achieve the above object. As a result, the present inventors have found that the skin permeability of lidocaine is further improved by a lidocaine-containing hydrogel patch comprising: a support layer; a adhesive layer stacked on a surface of the support layer, wherein the adhesive layer comprises at least one selected from the group consisting of lidocaine and pharmaceutically acceptable salts thereof, a total content of the lidocaine and the pharmaceutically acceptable salts thereof in the adhesive layer is in a specific range, and a pH of the adhesive layer is in a specific range. Moreover, the present inventors have found that the precipitation of crystals of lidocaine over time is suppressed to some degree by adjusting the pH of the adhesive layer, but the adjustment of pH alone does not always prevent the precipitation of lidocaine. The present inventors have further advanced the study on the basis of such findings. As a result, it has been found that, astonishingly, the precipitation of lidocaine can be sufficiently suppressed by causing a specific amount of oleic acid, which is ordinarily used as a percutaneous absorption accelerator, to be contained in the adhesive layer, and by adjusting the pH of the adhesive layer. This finding has led to the completion of the present invention.

Specifically, a lidocaine-containing hydrogel patch of the present invention comprises:
a support layer; and
a adhesive layer stacked on a surface of the support layer, wherein
the adhesive layer comprises at least one selected from the group consisting of lidocaine and pharmaceutically acceptable salts thereof,
a total content of the lidocaine and the pharmaceutically acceptable salts thereof is 3 to 8% by mass relative to the entire mass of the adhesive layer,
the adhesive layer further comprises oleic acid in an amount of 0.3 to 1% by mass relative to the entire mass of the adhesive layer, and
a pH of the adhesive layer is 6.8 to 7.4.

The lidocaine-containing hydrogel patch of the present invention is preferably such that the adhesive layer further comprises an acid-treated gelatin, and is more preferably such that a content of the acid-treated gelatin is 1 to 5% by mass relative to the entire mass of the adhesive layer.

Advantageous Effects of Invention

The present invention makes it possible to provide a lidocaine-containing hydrogel patch which is excellent in the skin permeability of lidocaine, and which makes it possible to sufficiently suppress the precipitation of crystals of lidocaine over time.

BRIEF DESCRIPTION OF DRAWING

FIG. 1 is a graph showing results of a skin permeation test conducted on hydrogel patches obtained in Examples 6 and 8.

DESCRIPTION OF EMBODIMENTS

Hereinafter, the present invention will be described in detail on the basis of preferred embodiments thereof.

A lidocaine-containing hydrogel patch of the present invention comprises: a support layer, and a adhesive layer stacked on at least one surface (ordinarily on one surface) of the support layer.

The adhesive layer according to the present invention comprises at least one selected from the group consisting of lidocaine and pharmaceutically acceptable salts thereof. When the pharmaceutically acceptable salts of lidocaine are contained, the salts may be inorganic salts or organic salts, and preferably inorganic salts. Examples of the inorganic salts include monobasic acid salts such as hydrochloric acid salt, hydrobromic acid salt, and methane sulfonic acid salt; polybasic acid salts such as fumaric acid salt, maleic acid salt, citric acid salt, and tartaric acid salt.

In the adhesive layer according to the present invention, the total content of the lidocaine and the pharmaceutically acceptable salts thereof is 3 to 8% by mass relative to the entire mass of the adhesive layer. If the content is less than the lower limit, the skin permeability of lidocaine is reduced, so that the effect (efficacy) of lidocaine is not sufficiently exhibited. Meanwhile, if the content exceeds the upper limit, crystals of lidocaine precipitate over time during storage of the hydrogel patch. From the viewpoints of tendencies that the effect (efficacy) of lidocaine is further improved, and that the precipitation of crystals of lidocaine over time is more likely to be suppressed, the content is particularly preferably 4 to 6% by mass.

The adhesive layer according to the present invention further comprises oleic acid. When the adhesive layer comprises oleic acid, the precipitation of crystals of lidocaine over time is sufficiently suppressed. The content of oleic acid is 0.3 to 1% by mass relative to the entire mass of the adhesive layer. If the content is less than the lower limit, the effect of suppressing the precipitation of crystals of lidocaine is not sufficiently exhibited. Meanwhile, if the content exceeds the upper limit, the oleic acid easily separates from the adhesive layer to form a phase as an oil component. As a result, the adhesiveness of the adhesive layer is likely to be reduced, or the surface of the adhesive layer is likely to become sticky to cause unpleasant texture. From the viewpoint of a tendency that the precipitation of crystals of lidocaine is more suppressed, the content is particularly preferably 0.5 to 1% by mass. Note that the term "being sticky" in the present invention means that after a hydrogel patch is peeled from the skin, the stickiness remains on the surface of the skin.

Moreover, the pH of the adhesive layer according to the present invention is 6.8 to 7.4. If the pH is less than the lower limit, the skin permeability of lidocaine is reduced. Meanwhile, if the pH exceeds the upper limit, the solubility of lidocaine in the adhesive layer is reduced, so that crystals are more likely to precipitate. When the adhesive layer comprises the acid-treated gelatin to be described below, the pH is particularly preferably 7.0 to 7.4 from the viewpoint of further improvement of the skin permeability of lidocaine.

Note that, in the present invention, the pH of the adhesive layer can be determined as follows. Specifically, a dispersion of the adhesive layer is obtained by adding 19 g of purified water to 1 g of the adhesive layer sampled from the hydrogel patch, followed by sufficient mixing. Then, the pH of the dispersion is measured by use of a glass electrode and a reference electrode according to the pH determination described in General Tests, Processes and Apparatus of The Japanese Pharmacopoeia (The Japanese Pharmacopoeia Fifteenth Edition).

The adhesive layer according to the present invention preferably further comprises water, a polyvalent alcohol, and a water-soluble polymer, in addition to lidocaine, the pharmaceutically acceptable salts thereof, and oleic acid.

The quality of the water is not particularly limited. The water is preferably water subjected to purification such as ion exchange, distillation, and filtration, and, for example, "Purified Water" described in The Japanese Pharmacopoeia (The Japanese Pharmacopoeia Fifteenth Edition) can be used suitably.

The content of the water is 19.85% by mass or more and less than 30% by mass (specifically 19.85 to 29.99% by mass), and more preferably 19.85 to 29.85% by mass, relative to the entire mass of the adhesive layer. A content of the water within the range leads to tendencies that the precipitation of crystals of lidocaine are more suppressed, that the water content in the obtained hydrogel patch is stabilized because the loss of water due to volatilization is limited during production process, and moreover that water is more stably retained during storage of the hydrogel patch. In addition, a content of water within the above-described range leads to a tendency that the amount of the change in temperature of the hydrogel patch due to latent heat of vaporization of water is reduced in the course of establishing the equilibrium of water between the hydrogel patch and the atmosphere (the equilibrium between the loss due to vaporization and the absorption of moisture). Moreover, for example, it is possible to prevent an unintended cold stimulation when the hydrogel patch of the present invention is pasted onto a site affected by postherpetic neuralgia (PHN).

If the content of water exceeds the upper limit, crystals of lidocaine tend to precipitate more easily. Moreover, since water volatilizes through the support layer of the hydrogel patch being pasted, the characteristic of the adhesive tend to change greatly. Specifically, even when the hydrogel patch has favorable pasting characteristics soon after being pasted, the following problems tend to be caused. For example, water in the adhesive layer volatilizes 5 to 12 hours after the pasting. As a result, the adhesive characteristics of the adhesive layer changes, so that, when the hydrogel patch is peeled, an unexpected force acts on the skin at an affected site to cause pain, or so that the adhesiveness of the adhesive layer is reduced. Moreover, the flexibility of the adhesive layer is reduced, so that the followability to the expansion and contraction of the skin is lowered, or the hydrogel patch becomes more likely to peel off. Moreover, when the content of water exceeds the upper limit, an increased amount of water is lost due to vaporization, so that the cold stimulation of the hydrogel patch tends to be increased. As a result, a strong stimulation may be given to PHN patients, who feel pain in an amplified manner because of sensitization of sensory nerves. On the other hand, when the content of water is less than the lower limit, the cold stimulation as described above tends to be reduced. However, the pain given to the skin at the affected site when the hydrogel patch is peeled tends to be increased. Moreover, if the content of water is less than the lower limit, for example, the following problem tends to be caused. Specifically, when a cross-linking agent comprising, for example, a multivalent metal salt for the cross-linking of the water-soluble polymer, and the like are added, the cross-linking agent and the like cannot sufficiently dissolve in water, so that the adhesive layer is not sufficiently cross-linked, and only the adhesive layer remains on the skin when the hydrogel patch is peeled.

Examples of the polyvalent alcohol include glycerin, propylene glycol, polyethylene glycol, butylene glycol, sorbitol, and the like. One of or a combination of two or more of these polyvalent alcohols may be used as the polyvalent alcohol. When the adhesive layer comprises such a polyvalent alcohol, the content of the polyvalent alcohol is preferably 10 to 70% by mass relative to the entire mass of the adhesive layer from the viewpoint that a preferred water retention ability, a preferred drug solubility, and a preferred adhesiveness can be retained in a well balanced manner in the adhesive layer. In addition, of these polyvalent alcohols, glycerin and propylene glycol are preferably used.

The glycerin is not particularly limited, and an example thereof is "Concentrated Glycerin" described in The Japanese Pharmacopoeia (The Japanese Pharmacopoeia Fifteenth Edition). When the adhesive layer comprises glycerin, the content of glycerin is preferably 30 to 60% by mass relative to the entire mass of the adhesive layer. If the content is less than the lower limit, it tends to be difficult to dissolve the water-soluble polymer uniformly. Meanwhile, if the content exceeds the upper limit, it tends to be difficult to dissolve the water-soluble polymer sufficiently.

When the adhesive layer comprises the glycerin and the water, the mass ratio between water and glycerin (the mass of water contained:the mass of glycerin contained) is preferably 1:1 to 1:3, and more preferably in a range from 1:1.2 to 1:2. If the content of the glycerin with respect to the water is less than the lower limit, water in the adhesive layer becomes more likely to be lost due to vaporization. As a result, the cold stimulation of the hydrogel patch tends to be increased, and the adhesiveness of the adhesive layer tends to be reduced when the adhesive layer becomes dry. Meanwhile, if the content exceeds the upper limit, it becomes difficult to dissolve the water-soluble polymer sufficiently, although the cold stimulation of the adhesive layer tends to be reduced, and the adhesiveness tends to be kept for a long period because the adhesive layer becomes less likely to be dry.

An example of the propylene glycol is 1,2-propylene glycol among the structural isomers thereof. When the propylene glycol is contained, the content thereof is preferably 1 to 3 times the mass of the lidocaine in the adhesive layer. When the content is within the range, there is a tendency that the precipitation of crystals of lidocaine can be more suppressed. Moreover, it becomes easier to mix the oleic acid more uniformly in the adhesive layer without blending a surfactant, and the stickiness on the surface of the adhesive layer tends to be reduced.

Examples of the water-soluble polymer include polyacrylic acid salts, polyacrylic acid, carboxyvinyl polymer, carboxymethyl cellulose, carboxymethyl cellulose sodium, methyl cellulose, ethyl cellulose, hydroxyethyl cellulose, gelatin, casein, pullulan, agar, dextran, dextrin, sodium alginate, soluble starch, carboxylated starch, polyvinyl alcohol, polyethylene oxide, polyacrylic amide, polyvinylpyrrolidone, polyvinyl ether-maleic anhydride copolymer, methoxyethylene-maleic anhydride copolymer, isobutylene-maleic anhydride copolymer, polyethylenimine, and the like. One of or a combination of two or more of the water-soluble polymers may be used as the water-soluble polymer.

When the adhesive layer comprises such a water-soluble polymer, the content thereof is preferably 5 to 20% by mass relative to the entire mass of the adhesive layer, from the viewpoint that preferred physical properties as a gel (strength, resilience, durability, adhesiveness, water retaining ability, and the like) tend to be obtained. In addition, of these water-soluble polymers, gelatin, polyacrylic acid salts, and polyacrylic acid are preferably used.

The gelatin has an action of gelling the adhesive layer to thereby keep the shape of the adhesive layer. The gelatin may be obtained by using a raw material of any animal species such as cattle, pig, whale, or fish, and may be made of any part such as the skin, the bone, the ligament, or the tendon. The gelatin is a protein, and is produced as follows. Specifically, a crude collagen obtained by subjecting the bone, the skin or the like, which serves as the raw material, to an acid treatment using an inorganic acid such as hydrochloric acid or sulfuric acid, an alkali treatment using lime or the like, an enzyme treatment, or the like. The thus obtained crude collagen is then subjected to extraction with hot water, and the like. Examples of the gelatin include an acid-treated gelatin obtained by the acid treatment, an alkali-treated gelatin obtained by the alkali treatment, an enzymatically treated gelatin obtained by the enzymatic treatment, and the like. The acid-treated gelatin (Type A) generally has an isoelectric point in the range from pH 7 to 9, whereas the alkali-treated gelatin (Type B) generally has an isoelectric point in the range from pH 4 to 6.

The lidocaine-containing hydrogel patch of the present invention is preferably such that the adhesive layer further comprises the acid-treated gelatin, from the viewpoints that preferred physical properties as a gel is obtained, and that the skin permeability of lidocaine is further improved.

When the adhesive layer comprises the acid-treated gelatin, the content thereof is preferably 1 to 5% by mass relative to the entire mass of the adhesive layer, from the viewpoint that further preferred physical properties as a gel are obtained, and that the skin permeability of lidocaine is further improved.

Note that, although it is not exactly clear why the skin permeability of lidocaine is further improved by causing the adhesive layer further to comprise the acid-treated gelatin, the present inventors speculate as follows. Specifically, when the pH of the adhesive layer is about 7.0, almost no charges or positive charges are present on the molecules of the acid-treated gelatin, so that electrical interaction with the lidocaine cations is reduced. As a result, lidocaine is rapidly diffused to the skin side. On the other hand, when the alkali-treated gelatin is used, negative charges are present on the molecules of the alkali-treated gelatin, so that interaction electrically attracting the lidocaine cations occurs. As a result, the diffusion of lidocaine to the skin is suppressed.

The polyacrylic acid salt is a polymer (polyacrylic acid) which is obtained by polymerizing acrylic acid and whose carboxyl groups are completely or partially neutralized with a metal such as sodium, or with ammonium ions or the like. A polymer having a neutralization ratio of 0% is polyacrylic acid. A polymer having a neutralization ratio of 100% may be referred to as completely neutralized polyacrylic acid, and a polymer having a neutralization ratio of less than 100% may be referred to as partially neutralized polyacrylic acid. The neutralization ratio of the polyacrylic acid salt is preferably 30 to 100%.

When the adhesive layer comprises the polyacrylic acid salt, the content thereof is preferably 1 to 10% by mass relative to the entire mass of the adhesive layer, from the viewpoint that preferred physical properties as a gel tend to be obtained. When the adhesive layer comprises the polyacrylic acid, the content thereof is preferably 1 to 5% by mass relative to the entire mass of the adhesive layer, from the viewpoint that preferred physical properties as a gel tend to be obtained. When the adhesive layer comprises the polyacrylic acid salt and the polyacrylic acid, the total content thereof is preferably 2 to 13.5% by mass relative to the entire mass of the adhesive layer, from the viewpoint that more preferred physical properties as a gel tend to be obtained.

The adhesive layer according to the present invention may further comprises additives such as a cross-linking agent, a pH adjusting agent, a surfactant, a filler, a preservative, an antioxidant, and a chelating agent, as long as the effects of the invention are not inhibited.

The cross-linking agent has an action of gelling the adhesive layer through the cross-linking of the water-soluble polymer to thereby retain the shape of the adhesive layer. The cross-linking agent is not particularly limited, and examples thereof include multivalent metal salts such as aluminum.potassium sulfate, calcium chloride, magnesium chloride, aluminum hydroxide, dihydroxy aluminum aminoacetate, and magnesium aluminometasilicate. When the adhesive layer comprises the cross-linking agent, the content thereof is preferably 0.1 to 5% by mass relative to the entire mass of the adhesive layer, from the viewpoint that preferred physical properties as a gel are obtained.

Examples of the pH adjusting agent include organic acids such as acetic acid, lactic acid, oxalic acid, citric acid, tartaric acid, and edetic acid; inorganic acids such as hydrochloric acid, sulfuric acid, nitric acid, and phosphoric acid; pharmaceutically acceptable salts of the organic acids or the inorganic acids; and the like.

The adhesive layer according to the present invention preferably has a thickness of 250 to 1500 μm from the viewpoint of having preferred water retaining ability, cooling ability, and adhesiveness.

Since the precipitation of crystals of lidocaine is sufficiently suppressed in the adhesive layer according to the present invention, the adhesive layer is uniform even when observed with naked eyes after a certain time of period has elapsed, and no crystals of lidocaine are observed.

The material of the support layer according to the present invention is not particularly limited, and a material which can be generally used for a support layer of a hydrogel patch can be used as appropriate. Examples of the material include polyesters such as polyethylene, polypropylene, ethylene-vinyl acetate copolymer, polyvinyl chloride, polyurethane, polyethylene terephthalate, and polybutylene terephthalate; polyamides such as nylon; celluloses such as rayon, pulp, and cotton, and derivatives thereof; polyacrylonitrile; and the like. One of or a combination of two or more of these materials may be used as the material of the support layer. For the support layer according to the present invention, a fabric made of fibers of the above-described material is preferably used. It is more preferable to use as the fabric a nonwoven fabric obtained by processing the fibers by a method such as entanglement, thermal melt-bonding, press bonding, binder bonding, or the like.

For example, a nonwoven fabric made of polyester fibers is preferably used as the support layer. The mass per unit area of the nonwoven fabric is more preferably 50 to 200 g/m$^2$. If the mass per unit area of the nonwoven fabric is less than the lower limit, for example, a problem tends to occur that the hydrogel patch is easily ripped when being peeled, and seepage of the ingredients contained in the adhesive layer to the back surfaces of the support layer tends to cause deterioration in appearance and in feel of use of the hydrogel patch. Meanwhile, if the mass per unit area exceeds the upper limit, the stretchability and flexibility of the support layer become insufficient, so that the hydrogel patch tends to easily peel off.

The lidocaine-containing hydrogel patch of the present invention may further comprises a release liner layer to cover and protect the surface of the adhesive layer until the hydrogel patch is used. The material of the release liner layer is not particularly limited, and a material which can be used generally as a material for a release liner layer of a hydrogel patch can be used as appropriate. Examples of the material include polyesters such as polyethylene, polypropylene, ethylene-vinyl acetate copolymer, ethylene-vinyl alcohol copolymer, polyvinyl chloride, polyurethane, polyethylene terephthalate, polybutylene terephthalate, and polyethylene naphthalate; polyamides such as nylon; polyacrylonitrile; celluloses and derivatives thereof; foils of metals such as aluminum; and the like. One of or a combination of two or more of these materials may be used as the material of the release liner layer. Examples of the release liner layer include films and sheets made of the above-described materials. In such a film or a sheet, a surface to be in contact with the adhesive layer may be subjected in advance to a silicone treatment, a Teflon (registered trademark) treatment, or the like in order to enhance the releasability thereof. In addition, the thickness of the release liner layer is preferably in the range from 20 to 150 μm.

As the release liner layer, a film made of polyethylene terephthalate or polypropylene is preferably used, a polypropylene film (PP film) is more preferably used, and a non-oriented polypropylene film or a monoaxially oriented polypropylene film is particularly preferably used. If crystals of lidocaine precipitate from the adhesive layer of the hydrogel patch, the crystals are likely to be adhered to the PP film which is not subjected to a treatment to provide releasability. Hence, when the PP film is peeled from the adhesive layer, the film, which is normally transparent or translucent, is observed to be white and cloudy because of the crystals of lidocaine. Accordingly, it is possible to easily determine whether the crystals of lidocaine precipitate or not without using a microscope. A hydrogel patch in which crystals of lidocaine precipitate is unsuitable for use because the skin permeability of lidocaine thereof is poor. In this respect, the use of the PP film as the release liner layer allows ordinary users to determine easily whether the hydrogel patch is suitable or unsuitable for use.

The lidocaine-containing hydrogel patch of the present invention can be produced, for example, by the following method. First, the aforementioned at least one selected from the group consisting of lidocaine and pharmaceutically acceptable salts thereof, the oleic acid, and if needed, the water, the polyvalent alcohol, the water-soluble polymer, and the additives are kneaded with each other in a usual manner to obtain a homogeneous adhesive layer composition. Subsequently, the adhesive layer composition is applied onto at least one surface of the support layer (ordinarily on one surface). Thus, a adhesive layer having a predetermined thickness is formed. Subsequently, the release liner layer is pasted on a surface opposite to the support layer of the adhesive layer. Then, the stacked layers are cut into a predetermined shape. Thus, the lidocaine-containing hydrogel patch of the present invention can be obtained. Alternatively, the lidocaine-containing hydrogel patch of the present invention may be obtained as follows. Specifically, the adhesive layer composition is first applied onto one surface of the release liner layer. Thus, the adhesive layer having a predetermined thickness is formed. Then, the support layer is pasted on a surface opposite to the release liner layer of the adhesive layer, and the stacked layers are cut into a predetermined shape.

EXAMPLES

Hereinafter, the present invention will be described more specifically on the basis of Examples and Comparative Examples. However, the present invention is not limited to the following Examples. Note that the hydrogel patch obtained in each of Examples and Comparative Examples was subjected to a pH measurement of the adhesive layer, a skin permeation test, and a test for evaluating precipitation of crystals of lidocaine which were conducted in the following methods.

(pH Measurement of Adhesive Layer)

First, 1 g of the adhesive layer of the hydrogel patch was sampled, and 19 g of water was added to the sample, followed by sufficient mixing to thereby suspend the adhesive layer. Thus, a test liquid was obtained. Subsequently, the pH of the test liquid was determined by use of a glass electrode and a reference electrode according to the pH determination described in General Tests, Processes and Apparatus of The Japanese Pharmacopoeia (The Japanese Pharmacopoeia Fifteenth Edition). The thus determined pH was employed as the pH of the adhesive layer.

(Skin Permeation Test (In Vitro))

First, the skin on the back of a hairless mouse was peeled, and mounted on a Franz-type flow-through cell in which hot water of 37° C. was circulated through an outer peripheral portion, while the dermis side of the skin was located on the receptor chamber side. Subsequently, the hydrogel patch which was cut into a size of 5 cm$^2$ and had the release liner layer removed was pasted on the corneum side of the skin. A phosphate buffer solution was caused to flow through the receptor chamber of the flow-through cell at a constant flow volume. A sample liquid was collected every two hours from the receptor chamber for 20 hours. For each of the collected sample liquids, the concentration of the drug (lidocaine) was quantitatively determined by high-performance liquid chromatography. The amount of the drug permeating through the skin was determined for each duration, and the permeation rate (Flux: $\mu g/cm^2/hr$) of the drug was calculated by use of the following formula:

Flux($\mu g/cm^2/hr$)=[Drug concentration($\mu g/ml$)×Flow volume(ml)]/Hydrogel patch area(cm$^2$)/Time(hr)

In addition, the accumulative skin permeation amount ($\mu g/cm^2/12$ hr) of the drug in the 12 hours from the beginning was determined by summing up the permeation amounts of the drug in the 12 hours which were determined from the permeation rates obtained by the above-described formula. A pharmaceutical preparation having a large value of the permeation rate or the accumulative skin permeation amount can be regarded as one having an excellent skin permeability of the drug.

(Test for Evaluating Precipitation of Crystals of Lidocaine)

A hydrogel patch was stored in an oven at a temperature of 50° C. for two weeks. Then, the presence or absence of crystals of lidocaine precipitated on a surface of the adhesive layer of the hydrogel patch was observed with naked eyes, and evaluated on the basis of the following criteria:

Present: Crystals of lidocaine precipitated, and the release liner layer became white and cloudy.

Absent: The release liner layer remained transparent, and no crystals of lidocaine were observed.

Example 1

First, a adhesive layer composition was obtained by weighting and then mixing the ingredients described in Table 1 at the ratio described in Table 1. Subsequently, the obtained adhesive layer composition was spread on a surface of a polyester nonwoven fabric (mass per unit area: 100 g/m$^2$) at 1000 g/m$^2$, and then the surface on which the adhesive layer composition was applied was covered with a polypropylene release liner layer (which is not subjected to a treatment to provide releasability), and cut into a predetermined size (10 cm×14 cm). Thus, a hydrogel patch was obtained.

Examples 2 to 4 and Comparative Example 1

Each hydrogel patch was obtained in the same manner as in Example 1, except that the constitution of the adhesive layer composition was changed to the corresponding constitution shown in Table 1. Each of the hydrogel patches obtained in Examples 1 to 4 and Comparative Example 1 was subjected to the pH measurement of the adhesive layer and the skin permeation test. Table 1 shows the pH and the accumulative skin permeation amount ($\mu g/cm^2/12$ hr) of the adhesive layer of each hydrogel patch, as well as the constitution of each adhesive layer composition. Note that, in Tables 1 to 3, "Example" is abbreviated to "Ex.", and "Comparative Example" is abbreviated to "Comp Ex.".

TABLE 1

|  | Comp. Ex. 1 | Ex. 1 | Ex. 2 | Ex. 3 | Ex. 4 |
| --- | --- | --- | --- | --- | --- |
| Lidocaine (parts by mass) | 5.0 | 5.0 | 5.0 | 5.0 | 5.0 |
| 1,2-Propylene glycol (parts by mass) | 10.0 | 10.0 | 10.0 | 10.0 | 10.0 |
| Concentrated Glycerin (parts by mass) | 49.7 | 49.9 | 42.65 | 42.95 | 43.2 |
| Acid-treated gelatin (parts by mass) | 2.5 | 2.5 | 2.5 | 2.5 | 2.5 |
| Polyacrylic acid and polyacrylic acid salt (Total parts by mass) | 5.5 | 5.5 | 4.8 | 4.5 | 4.2 |
| Polyvinyl alcohol (parts by mass) | 1.0 | 1.0 | 1.0 | 1.0 | 1.0 |
| Oleic acid (parts by mass) | — | 0.5 | 0.5 | 0.5 | 0.5 |
| Cross-linking agent (parts by mass) | 3.0 | 3.0 | 1.0 | 1.0 | 1.0 |
| pH adjusting agent (parts by mass) | 1.3 | 0.6 | 0.55 | 0.55 | 0.6 |
| Filler (parts by mass) | 2.0 | 2.0 | 2.0 | 2.0 | 2.0 |
| Preservative (parts by mass) | 0.15 | 0.15 | 0.15 | 0.15 | 0.15 |
| Purified water (parts by mass) | 19.85 | 19.85 | 29.85 | 29.85 | 29.85 |
| Total (parts by mass) | 100 | 100 | 100 | 100 | 100 |
| pH of adhesive layer | 6.4 | 6.9 | 7.1 | 7.3 | 7.4 |
| Accumulative skin permeation amount ($\mu g/cm^2/12$ hr) | 93 | 213 | 271 | 337 | 351 |

As is apparent from the results shown in Table 1, it was found that the hydrogel patch of the present invention was excellent in the skin permeability of lidocaine, and the permeability was further improved as the pH increased. In contrast, it was found that the hydrogel patch (Comparative Example 1) which comprised no oleic acid and had a low pH of the adhesive layer was inferior in the skin permeability of lidocaine.

Examples 5 to 8 and Comparative Examples 2 to 4

Each hydrogel patch was obtained in the same manner as in Example 1, except that the constitution of the adhesive layer composition was changed to the corresponding constitution shown in Table 2 or 3. Each of the hydrogel patches obtained in Examples 5 to 7 and Comparative Examples 2 to 4 was subjected to the pH measurement of the adhesive layer and the test for evaluating precipitation of crystals of lidocaine. Table 2 shows the results of the pH measurement of the adhesive layer and the test for evaluating precipitation of crystals of lidocaine which were conducted on each of the hydrogel patches obtained in Examples 5 to 7 and Comparative Example 2 to 4, as well as the constitution of each adhesive layer composition. Note that, no crystals of lidocaine were observed in any one of the hydrogel patches immediately after the production.

Meanwhile, each of the hydrogel patches obtained in Examples 6 and 8 was subjected to the pH measurement of the adhesive layer and the skin permeation test. Table 3 shows the results of the pH measurement of the adhesive layer conducted on each of the hydrogel patches obtained in Examples 6 and 8, as well as the constitution of each adhesive layer composition. FIG. 1 shows the results of the skin permeation test conducted thereon.

TABLE 2

|  | Comp. Ex. 2 | Comp. Ex. 3 | Ex. 5 | Ex. 6 | Ex. 7 | Comp. Ex. 4 |
| --- | --- | --- | --- | --- | --- | --- |
| Lidocaine (parts by mass) | 5.0 | 5.0 | 5.0 | 5.0 | 5.0 | 5.0 |
| 1,2-Propylene glycol (parts by mass) | 10.0 | 10.0 | 10.0 | 10.0 | 10.0 | 10.0 |
| Concentrated Glycerin (parts by mass) | 50.6 | 50.3 | 50.1 | 49.9 | 49.4 | 38.55 |
| Acid-treated gelatin (parts by mass) | 2.5 | 2.5 | 2.5 | 2.5 | 2.5 | 2.5 |
| Polyacrylic acid and polyacrylic acid salt (Total parts by mass) | 5.5 | 5.5 | 5.5 | 5.5 | 5.5 | 4.2 |
| Polyvinyl alcohol (parts by mass) | 1.0 | 1.0 | 1.0 | 1.0 | 1.0 | 1.0 |
| Oleic acid (parts by mass) | — | 0.1 | 0.3 | 0.5 | 1.0 | — |
| Surfactant (parts by mass) | — | — | — | — | — | 1.0 |
| Cross-linking agent (parts by mass) | 3.0 | 3.0 | 3.0 | 3.0 | 3.0 | 5.0 |
| pH adjusting agent (parts by mass) | 0.4 | 0.6 | 0.6 | 0.6 | 0.6 | 0.6 |
| Filler (parts by mass) | 2.0 | 2.0 | 2.0 | 2.0 | 2.0 | 2.0 |
| Preservative (parts by mass) | 0.15 | 0.15 | 0.15 | 0.15 | 0.15 | 0.15 |
| Purified water (parts by mass) | 19.85 | 19.85 | 19.85 | 19.85 | 19.85 | 30.00 |
| Total (parts by mass) | 100 | 100 | 100 | 100 | 100 | 100 |
| pH of adhesive layer | 7.0 | 6.9 | 6.9 | 6.9 | 6.9 | 8.5 |
| Evaluation of precipitation of lidocaine crystals | Present | Present | Absent | Absent | Absent | Present |

TABLE 3

|  | Ex. 6 | Ex. 8 |
| --- | --- | --- |
| Lidocaine (parts by mass) | 5.0 | 5.0 |
| 1,2-Propylene glycol (parts by mass) | 10.0 | 10.0 |
| Concentrated Glycerin (parts by mass) | 49.9 | 49.9 |
| Acid-treated gelatin (parts by mass) | 2.5 | — |
| Alkali-treated gelatin (parts by mass) | — | 2.5 |
| Polyacrylic acid and polyacrylic acid salt (Total parts by mass) | 5.5 | 5.5 |
| Polyvinyl alcohol (parts by mass) | 1.0 | 1.0 |
| Oleic acid (parts by mass) | 0.5 | 0.5 |
| Cross-linking agent (parts by mass) | 3.0 | 3.0 |
| pH adjusting agent (parts by mass) | 0.6 | 0.6 |
| Filler (parts by mass) | 2.0 | 2.0 |
| Preservative (parts by mass) | 0.15 | 0.15 |
| Purified water (parts by mass) | 19.85 | 19.85 |
| Total (parts by mass) | 100 | 100 |
| pH of adhesive layer | 6.9 | 6.9 |

As is apparent from the results shown in Table 2, no particular change from the state immediately after the production was observed in each hydrogel patch of the present invention, and it was found that the precipitation of the crystals of lidocaine over time was sufficiently suppressed. In contrast, it was found that the precipitation of the crystals of lidocaine over time was difficult to suppress in each of the hydrogel patches which comprised no oleic acid, or a small amount of oleic acid (Comparative Examples 2 to 4). In particular, it was found that the precipitation of crystals of lidocaine over time tended to easily occur in the hydrogel patch which comprised no oleic acid, had a high pH of the adhesive layer, and had a high content of water (purified water) in the adhesive layer (Comparative Example 4).

In addition, as is apparent from the results shown in Table 3 and FIG. 1, it was found that, as for the hydrogel patches of the present invention, the skin permeability of lidocaine was more improved in the case where an acid-treated gelatin was used (Example 6) than in the case where an alkali-treated gelatin was used (Example 8).

INDUSTRIAL APPLICABILITY

As described above, it is possible to provide a lidocaine-containing hydrogel patch which is excellent in the skin permeability of lidocaine, and which makes it possible to sufficiently suppress the precipitation of crystals of lidocaine over time.

The invention claimed is:

1. A hydrogel patch comprising a support layer and an adhesive layer;
   wherein the adhesive layer comprises acid-treated gelatin, 3 to 8 mass % lidocaine or a pharmaceutically acceptable salt thereof, and 0.3 to 1 mass % of an oleic acid based on the mass of the adhesive layer;
   wherein the adhesive layer has a pH ranging from 6.8 to 7.4; and
   wherein the precipitation of lidocaine in the adhesive layer of the hydrogel patch after storage of the patch at 50° C. for two weeks is less than that in an otherwise identical patch having an adhesive layer that does not contain oleic acid.

2. The hydrogel patch according to claim 1, wherein the adhesive layer comprises 4 to 6 mass % of lidocaine or a pharmaceutically acceptable salt thereof.

3. The hydrogel patch according to claim 1, wherein the adhesive layer contains 0.5 to 1 mass % of the oleic acid.

4. The hydrogel patch according to claim 1, wherein the adhesive layer contains 1 to 5 mass % of the acid-treated gelatin.

5. The hydrogel patch according to claim 1, wherein the adhesive layer has a pH ranging from 7.0 to 7.4.

6. The hydrogel patch according to claim 1, wherein the adhesive layer comprises water in an amount ranging from 19.85 to less than 30 mass %.

7. The hydrogel patch according to claim 1, wherein the adhesive layer comprises a polyvalent alcohol or a water-soluble polymer, or both.

8. The hydrogel patch according to claim 1, wherein the adhesive layer comprises at least one polyvalent alcohol selected from the group consisting of glycerol, propylene glycol, polyethylene glycol, butylene glycol and sorbitol.

9. The hydrogel patch according to claim 1, wherein the adhesive layer comprises at least one polyvalent alcohol selected from the group consisting of glycerol, propylene glycol, polyethylene glycol, butylene glycol and sorbitol in an amount ranging from 10 to 70 mass % based on the mass of the adhesive layer.

10. The hydrogel patch according to claim 1, wherein the adhesive layer comprises glycerin and water in a mass ratio ranging from 1:1 to 1:3.

11. The hydrogel patch according to claim 1, wherein the adhesive layer comprises glycerin and water in a mass ratio ranging from 1:1.2 to 1:2.

12. The hydrogel patch according to claim 1, wherein the adhesive layer comprises propylene glycol in an amount ranging from 1 to 3 times the mass of the lidocaine in the adhesive layer.

13. The hydrogel patch according to claim 1, wherein the adhesive layer comprises propylene glycol in an amount ranging from 1 to 3 times the mass of the lidocaine in the adhesive layer; wherein said adhesive layer does not contain a surfactant.

14. The hydrogel patch according to claim 1, wherein the adhesive layer comprises at least one water-soluble polymer selected from the group consisting of polyacrylic acid salts, polyacrylic acid, carboxyvinyl polymer, carboxymethyl cellulose, carboxymethyl cellulose sodium, methyl cellulose, ethyl cellulose, hydroxyethyl cellulose, gelatin, casein, pullulan, agar, dextran, dextrin, sodium alginate, soluble starch, carboxylated starch, polyvinyl alcohol, polyethylene oxide, polyacrylic amide, polyvinylpyrrolidone, polyvinyl ether-maleic anhydride copolymer, methoxyethylene-maleic anhydride copolymer, isobutylene-maleic anhydride copolymer, and polyethylenimine; or a mixture thereof.

15. The hydrogel patch according to claim 1, wherein the adhesive layer comprises at least one water-soluble polymer in an amount ranging from 5 to 20 mass %.

16. The hydrogel patch according to claim 1, wherein the adhesive layer comprises Type A acid-treated gelatin having an isoelectric point ranging from pH 7 to pH 9.

17. The hydrogel patch according to claim 1, wherein the adhesive layer comprises 1 to 10 mass % of a polyacrylic salt, 1 to 5 mass % of a polyacrylic acid, or 2 to 13.5 mass % of the polyacrylic salt and the polyacrylic acid, and comprises Type A acid-treated gelatin having an isoelectric point ranging from pH 7 to pH 9.

18. The hydrogel patch of claim 1, wherein thickness of the adhesive layer ranges from 250 to 1,500 μm.

19. The hydrogel patch of claim 1, further comprising a release liner layer.

20. A method for suppressing precipitation of lidocaine in a hydrogel patch comprising a support layer and an adhesive layer;
    wherein the adhesive layer comprises acid-treated gelatin, 3% to 8% mass lidocaine or a pharmaceutically acceptable salt thereof, and wherein the adhesive layer has a pH ranging from 6.8 to 7.4;
    comprising the step of incorporating oleic acid into said adhesive layer of the patch in an amount between 0.3% to 1% based on the mass of the adhesive layer.

* * * * *